United States Patent [19]

Davies et al.

[11] 4,451,683

[45] May 29, 1984

[54] CATALYST, CATALYST SUPPORT AND OXYCHLORINATION PROCESS

[75] Inventors: Phineas Davies, Middlesbrough; James R. Jennings, Yarm; Jack Wolstenholme, Northwich, all of England

[73] Assignee: Imperial Chemical Industries PLC, London, England

[21] Appl. No.: 337,998

[22] Filed: Jan. 8, 1982

[30] Foreign Application Priority Data

Jan. 15, 1981 [GB] United Kingdom ................. 8101137
Jul. 14, 1981 [GB] United Kingdom ................. 8121714

[51] Int. Cl.$^3$ ............................................ C07C 17/02
[52] U.S. Cl. .................................... 570/224; 570/243; 570/248; 502/225; 502/244; 502/341; 502/345; 502/346
[58] Field of Search ............... 252/441, 443, 475, 476; 570/243, 248, 251, 224, 225, 245

[56] References Cited

U.S. PATENT DOCUMENTS

| | | | |
|---|---|---|---|
| 3,579,597 | 5/1971 | Antonini et al. | 252/441 |
| 3,624,170 | 11/1971 | Wakiyama et al. | 252/441 |
| 3,709,950 | 1/1973 | Baker et al. | 570/224 |
| 3,720,723 | 3/1973 | Pritchett | 570/243 |
| 3,992,462 | 11/1976 | Antonini et al. | 570/243 |
| 4,069,170 | 1/1978 | Blake et al. | 252/441 |
| 4,194,990 | 3/1980 | Pieter et al. | 252/441 |
| 4,273,678 | 6/1981 | Lane et al. | 570/243 |
| 4,300,005 | 11/1981 | Li | 570/243 |
| 4,323,716 | 4/1982 | Canavesi et al. | 252/441 |

FOREIGN PATENT DOCUMENTS

780498 3/1968 Canada ................................ 570/243

OTHER PUBLICATIONS

Handbook of Chemistry and Physics (CRC), 1976, 57th Ed., pp. B–86, 127, 128.

*Primary Examiner*—Delbert E. Gantz
*Assistant Examiner*—A. Pal
*Attorney, Agent, or Firm*—Cushman, Darby & Cushman

[57] ABSTRACT

An oxychlorination catalyst contains a copper compound, magnesium oxide and aluminium oxide, and the copper compound is present as a distinct phase on a support in which at least part of the magnesium oxide is in combined form with alumina.

13 Claims, 1 Drawing Figure

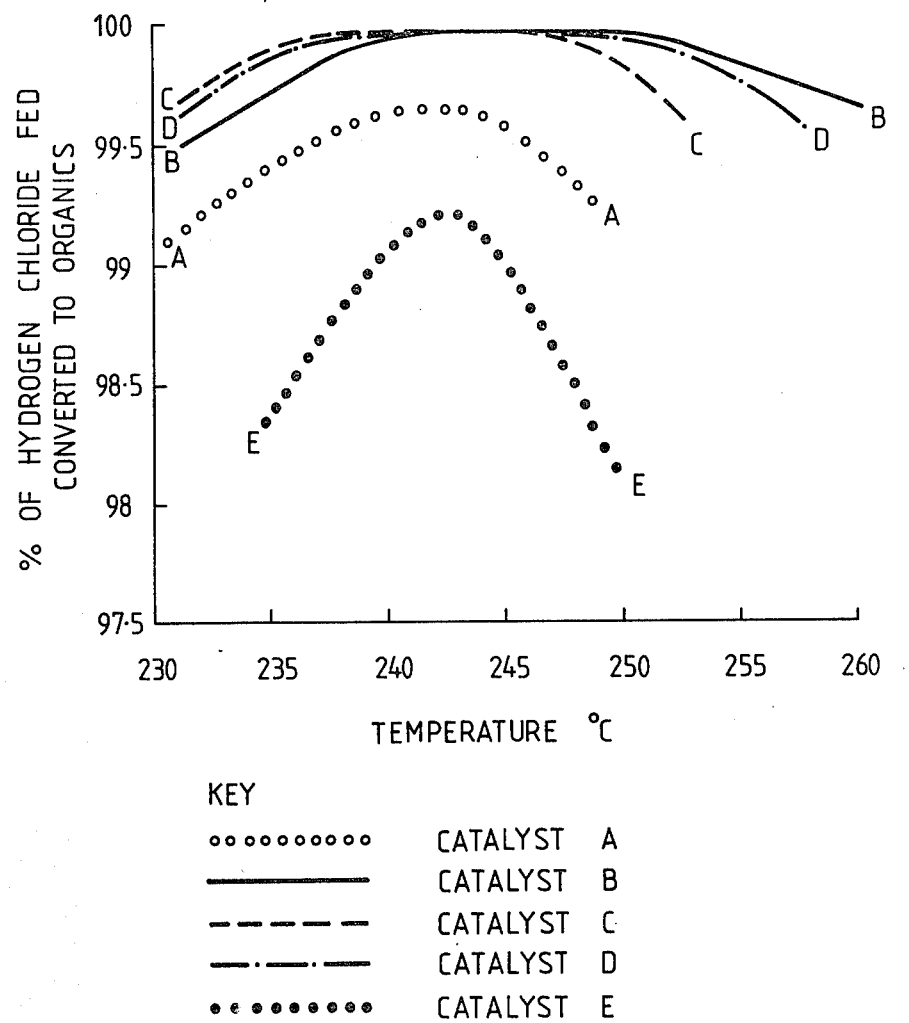

CATALYST, CATALYST SUPPORT AND OXYCHLORINATION PROCESS

This invention relates to a catalyst, a catalyst support, the preparation thereof and the use of the catalyst in the oxychlorination of ethylene.

In U.K. Specification No. 1,345,653 there is described a catalyst consisting of copper and magnesium in the form of their chlorides supported on active alumina of specified surface area, but devoid of alkali metal compounds, which are stated to have a tendency to reduce the activity of the catalyst.

In our U.K. Pat. No. 1,439,171 there is described an oxychlorination process using as catalyst an intimate mixture of the oxides of magnesium, aluminium and copper. In our U.K. Pat. No. 1,439,172 there is described a method of making such a catalyst in which the aluminium oxide is formed by calcination of a precursor thereof in the presence of a precursor of magnesium oxide; the desired intimate mixture may be prepared by co-precipitation of the hydroxides of magnesium, aluminium and copper, followed by calcination of the mixture of hydroxides thus obtained. An alternative method described is firstly to prepare an intimate mixture of the oxides of magnesium and aluminium and then to introduce copper into the oxide lattice by ion exchange with an aqueous solution of copper nitrate.

According to the present invention there is provided an oxychlorination catalyst composition containing a copper compound, magnesium oxide and aluminium oxide, characterised in that the copper compound is present on a support comprising magnesium oxide and aluminium oxide, at least part of the magnesium oxide being present in combined form in the support.

The copper compound content of the catalyst composition is preferably at least 1% (for example 1 to 15, especially 4 to 12%) by weight calculated as Cu on the total of catalyst constituents not volatile at 300° C. The copper compound is present as a distinct phase.

The copper compound is preferably copper chloride or one or more compounds convertible to copper chloride during oxychlorination, for example the oxide, hydroxide, basic chloride, other halides, carbonate, carboxylate or nitrate.

The phase containing the copper compound preferably also contains one or more compounds of one or more alkali metals, especially potassium. The alkali metal is preferably accompanied by at least an equivalent proportion of chloride ions. Especially when an alkali metal chloride is present at least part of the copper may be present in anionic form, as in the compounds represented by the formula $KCuCl_3$ or $K_2CuCl_4$.

The number of ions of alkali metal is preferably not more than 100 per 100 of copper. It is especially preferred that the number of ions of alkali metal is not more than 50 per 100 of copper, for example 2 to 50, especially 5 to 35.

Compounds of other metals may also be present in the phase containing copper; these include especially rare earth metals, the concentration of which is suitably in the range 0.1 to 2.0% by weight of the catalyst, calculated as equivalent $CeCl_3$.

The proportion of magnesium oxide to aluminium oxide is preferably in the range 0.2 to 2.5 mols of MgO per mol of $Al_2O_3$. In general, a suitable range of proportions is 0.2 to 1.6, especially 0.3 to 1.1 mol, of MgO per mol of $Al_2O_3$; relatively higher proportions of MgO within the range up to 2.5 mols of MgO per mol of $Al_2O_3$ may, however, be used especially when the conditions of operation of the oxychlorination process are such that a catalyst of relatively lower activity is acceptable or desirable (for example when operating at relatively high temperatures).

In preferred catalysts the surface area is at least 50, preferably at least 70 and up to 200 especially in the range 80–160, $m^2g^{-1}$, as measured by adsorption of nitrogen at 77.35° K., 760 mm pressure, using a Model 2200 High Speed Surface Area Analyser supplied by Micromeritics Instrument Corporation of Norcross, Georgia, USA.

The catalyst may be in the form of fluidisable particles, suitably having diameters in the range 10 to 300 microns and with an appropriate diameter distribution.

Alternatively the catalyst may be in a form suitable for use in a fixed bed, for example cylinders, rings, spheres or approximate spheres, having dimensions in the range from 2 to 20 mm.

The pore volume of the catalyst is preferably in the range 0.2 to 1.0 $cm^3g^{-1}$.

The catalyst bed may comprise two or more of the catalysts of the present invention, the said catalysts differing in composition. Alternatively or additionally one or more of the catalysts may be mixed with non-catalytic particles of refractory material. By this means a catalyst bed of controlled uniform or graded catalyst activity can be set up.

The surface area of the magnesia/alumina support is preferably in the range 120 to 250, especially over 150, for example 160 to 200 $m^2g^{-1}$. Its pore volume is preferably in the range 0.5 to 1.5 ml $g^{-1}$. Thus it will be noted that the surface area and pore volume of the oxychlorination catalyst are less than those of the support from which it is made.

The support comprising magnesium oxide and aluminium oxide (wherein at least part of the magnesium oxide is present in combined form) may be prepared by general methods. The preferred method of preparation involves co-precipitation from aqueous solutions of water-soluble salts, followed by drying and calcination to effect combination of magnesium and aluminium oxides. Thus, for example a water-soluble magnesium salt such as the nitrate may be reacted with an alkali-metal aluminate, these reactants containing an excess respectively of acid or of alkali appropriate to the required magnesia to alumina ratio.

Calcination is preferably carried out after shaping the support material, preferably at a temperature in the range 400° to 900° C., typically above 650° and especially 700° to 800° C. to give the required surface area. Within these ranges the temperature is generally higher the greater the $MgO/Al_2O_3$ ratio.

Impregnation of the support with the copper compound (and optionally the alkali-metal compound and/or the rare-earth compound) is carried out after calcination of the support material.

Impregnation is preferably carried out by contacting the support material with a volume of solution of the copper compound not more than sufficient to saturate the support. After application of the copper compound the product is dried, suitably at under 200° C., but is preferably not heated at over 300° C.

The catalysts of the invention may be used in the production of 1,2-dichloroethane by oxychlorination of ethylene using techniques and general reaction conditions well established in the art. Thus ethylene may be brought into contact with hydrogen chloride and molecular oxygen in the presence of the catalyst at an elevated temperature, for example in the range from 200° C. to 350° C., especially from 200° C. to 300° C. The molecular oxygen may be introduced as such or in the form of an oxygen-containing gas mixture, for example air. The pressure is suitably in the range 1–20 bar abs.

EXAMPLE 1
Catalyst support preparation

A solution of magnesium nitrate containing 9.9 g $l^{-1}$ MgO was made by dissolving light magnesium oxide in 55% w/w nitric acid: the acid was used at the rate of 4 molecules $HNO_3$ per mol of MgO in order to allow sufficient excess to react with the quantity of sodium aluminate to be used. A solution of sodium aluminate containing 47.6 g $l^{-1}$ of $Al_2O_3$ was made up by dissolving commercial stabilised sodium aluminate (empirical formula 1.1 $Na_2O.Al_2O_3$; stabiliser sorbitol) in water. Each solution was adjusted to 50° C. and pumped at equal flow rates through a small mixing vessel and thence into an ageing tank. The pH of the freshly mixed solutions was 9.5 at 50° C. The slurry accumulated in the ageing tank after 30 minutes' mixing was collected on a rotary filter. Twice the solid cake was scraped off the filter, re-slurried in a 1% solution of magnesium nitrate hexahydrate and collected on the filter. A sample of the filter cake was analysed for sodium and contained e.g. 0.3% w/w as $Na_2O$ on a loss-free basis. The filter cake was re-slurried in water at 7.0% w/w of solids. The slurry was spray dried by atomisation at a nozzle (outlet temperature 150° C.) to give a fine powder having a particle size range 20–200 microns, median 50–70 microns. The spray-dried powder was calcined at 730° C.

Table 1 shows the micromeritic properties of magnesia-alumina materials made by the above method. (The proportions of MgO, $Al_2O_3$ and $Na_2O$ present can be derived from Table 2 below).

TABLE 1

| Preparation | A | B | C | D |
|---|---|---|---|---|
| Surface area $m^2 g^{-1}$ | 183 | 161 | 157 | 179 |
| Pore volume $cm^3 g^{-1}$ | 0.85 | 0.81 | 0.84 | 0.60 |
| Helium density | 3.23 | 3.32 | 3.21 | 3.29 |
| Mercury density | 0.86 | 0.90 | 0.87 | 1.11 |
| Mean pore radius A | 90 | 100 | 110 | 65 |

Catalyst preparation

In each of four preparations 5.5 kg of the calcined particles were agitated in a mixer and sprayed with 2300 ml of a solution at 70° C. containing copper chloride dihydrate without or with potassium chloride. Heat was evolved as the alumina and magnesia absorbed water from the solution, causing precipitation of cupric chloride and/or potassium cupric chloride. The product was dried at 130° C., to give a khaki-brown powder containing a few loose agglomerates. It was transferred to air-tight containers.

The properties of the catalysts A–D, one made from each of the above supports A–D, are set out in Table 2, together with those of catalyst E, a comparison catalyst consisting of alumina-supported copper chloride and potassium chloride. For catalysts A–D the % w/w composition data refer to the catalyst as made; the balance up to 100% is mainly water of hydration.

Catalyst test

A 3.5 kg sample of each catalyst was tested in a semi-technical reactor 50 mm in diameter and 3 m high, with external cooling in an air jacket. The feed gas consisted of HCl, ethylene (5% excess) and air (20% oxygen excess) at a total pressure of 6.6 bar abs. The feed rate was maintained at about 3500 l $h^{-1}$, giving a contact time of about 15 seconds. The results (oxychlorination behaviour) are set out in Table 2 and represented in FIG. 1. Note: the numerical data for oxychlorination behaviour are believed to summarise the measured results of this test more representatively than those quoted in the specification of priority-founding U.K. application No. 8,101,137).

TABLE 2

| Catalyst | | A | B | C | D | E |
|---|---|---|---|---|---|---|
| Catalyst properties: | | | | | | |
| | MgO | 13.6 | 11.9 | 13.1 | 13.8 | — |
| | $Al_2O_3$ | 52.3 | 65.3 | 57.0 | 54.1 | 82.1 |
| | $Na_2O$ | 0.51 | 0.046 | 0.17 | 0.19 | 0.3 |
| % w/w | Cu | 10.9 | 6.4 | 6.5 | 7.0 | 6.9 |
| | Cl | 11.1 | 8.4 | 8.6 | 8.5 | 8.9 |
| | K | 0.0 | 1.2 | 1.2 | 0.39 | 1.8 |
| | loss at 900° C. | 22.6 | 14.7 | 11.1 | 14.1 | — |
| Molar ratio $MgO/Al_2O_3$ | | 0.65 | 0.41 | 0.5 | 0.64 | — |
| Atoms K per 100 atoms Cu | | 0 | 30 | 30 | 9.0 | 42 |
| Surface area, $m^2 g^{-1}$ | | 94.5 | 116 | 107 | 94 | 100 |
| Pore volume, $cm^3 g^{-1}$ | | 0.44 | 0.48 | 0.57 | 0.36 | 0.45 |
| Helium density | | 3.00 | 3.07 | 3.13 | 3.12 | — |
| Mercury density | | 1.29 | 1.24 | 1.13 | 1.48 | — |
| Mean pore radius, A | | 95 | 85 | 105 | 80 | — |
| Oxychlorination behaviour | | | | | | |
| Optimum temp °C. (To) | | 242 | 243–252 at least | 237–246 at least | 237–250 at least | 242 |
| Conversion of H Cl to organics at To, % | | 99.6 | 99.9 | 99.9 | 99.9 | 99.0 |
| Ethylene burn to CO and $CO_2$ at To, % | | 1.6 | 1.4–2.2 | 1.5–2.4 | 1.0–1.9 | 1.95 |
| 1,2-dichloroethylene purity % w/w at To | | 99.0 | 98.5–99.0 | 98.5–99.0 | 99.5 | 99.0 |

In each run the losses of copper chloride from the catalyst and of catalyst from the reactor were too low to measure.

The relationship between reaction temperature and conversion of HCl into organic products is shown in FIG. 1. The catalysts of the invention give excellent conversions. Furthermore, (especially with potassium containing catalysts B-D), the conversion is at or close to its maximum over a relatively wide range of temperature; this is an advantage in large scale operation since less precise temperature control is required and helps to make the analogous fixed bed process practicable.

EXAMPLE 2

Effects of higher magnesia content or of the presence of rare earth ("RE") chloride Five catalysts F-J were prepared by the methods described in Example 1 to test these effects. Their compositions and micromeritic properties are set out in Table 3, together with those of a commercially available catalyst K.

These catalysts were tested in a process similar to that described in Example 1, except that the pressure was atmospheric instead of 6.6 bar abs. Data showing the oxychlorination behaviour of catalysts F, H, J and K are set out in the second part of Table 3. It is evident that lanthanum broadens the temperature range over which optimum HCl conversion is obtained, but does not limit oxidation of ethylene to CO and $CO_2$ as effectively as potassium. Cerium-containing catalysts G and I were found to be similar to the corresponding lanthanum containing catalysts except that To was 5°–10° C. higher.

TABLE 3

| Catalyst | | F | G | H | I | J | K |
|---|---|---|---|---|---|---|---|
| Catalyst properties: | | | | | | | |
| % w/w | MgO | 17.0 | 11.5 | 11.5 | 11.9 | 11.3 | — |
| | $Al_2O_3$ | 58.6 | 65.0 | 63.8 | 65.5 | 65.1 | 82.1 |
| | $Na_2O$ | 1.1 | 0.09 | 0.08 | 0.08 | 0.08 | 0.3 |
| | Cu | 7.1 | 6.7 | 6.6 | 6.6 | 6.9 | 6.9 |
| | Cl | 8.2 | 8.4 | 8.4 | 7.9 | 8.0 | 8.9 |
| | K | 0.49 | 0.5 | 0.49 | 0.003 | 0.08 | 1.8 |
| | RE, as $CeCl_3$ | — | (Ce) 0.43 | (La) 0.71 | (Ce) 0.43 | (La) 0.71 | — |
| | loss at 900° C. | 18.4 | 15.9 | 15.6 | 15.4 | 15.2 | — |
| Molar ratio MgO/$Al_2O_3$ | | 0.73 | 0.45 | 0.46 | 0.46 | 0.44 | — |
| Atoms K per 100 atoms Cu | | 11.2 | 12.1 | 12.1 | — | 1.8 | 42 |
| Surface area, $m^2 g^{-1}$ | | 143.6 | 133.8 | 138.0 | 144.3 | 140.0 | 100 |
| pore volume, $cm^3 g^{-1}$ | | 0.48 | 0.44 | 0.45 | 0.55 | 0.46 | 0.45 |
| Helium density | | 3.18 | 3.14 | 3.13 | 3.23 | 3.19 | — |
| Mercury density | | 1.26 | 1.31 | 1.30 | 1.17 | 1.29 | — |
| Mean pore radius, A | | 67 | 66 | 65 | 76 | 66 | — |
| Oxychlorination behaviour | | | | | | | |
| Optimum temp °C. (To) | | 255–266 | — | 259–274 | — | 248–270 | 254 |
| Conversion of HCl to organics at To, % | | over 84 | — | over 84 | — | over 92 | 93.8 |
| Ethylene burn to CO and $CO_2$ at To, % | | 1.0–1.33 | — | 1.4–2.2 | — | 2.2–4.6 | 2.5 |
| DCE purity % w/w | | 98.8 | — | 98.5–97.8 | — | 94.2–99.3 | 98.8 |

We claim:

1. An oxychlorination catalyst comprising a copper compound, magnesium oxide and aluminium oxide, characterised in that the copper compound is present as a distinct phase on a support comprising magnesium oxide and aluminium oxide, at least part of said magnesium oxide being in chemical combination with said alumina as a result of calcination of said support at a temperature in the range 400°–900° C.

2. A catalyst according to claim 1 in which the proportion of magnesium oxide is in the range 0.2 to 1.6 mols of MgO per mol of $Al_2O_3$.

3. A catayst according to claim 2 in which the proportion of magnesium oxide is in the range 0.3 to 1.1 mols of MgO per mol of $Al_2O_3$.

4. A catalyst according to claim 1 in which the copper compound is copper chloride.

5. A catalyst according to claim 1 in which the phase containing the copper compound also contains an alkali metal compound.

6. A catalyst according to claim 5 in which the alkali metal is potassium.

7. A catalyst according to claim 5 in which the proportion of alkali metal is 2 to 50 ions per 100 ions of copper.

8. A catalyst according to claim 1 in which the phase containing copper also contains a compound of a rare earth metal.

9. A catalyst according to claim 8 in which the proportion of the rare earth metal compound is in the range 0.1 to 2.0% by weight, calculated as equivalent $CeCl_3$.

10. A catalyst according to claim 1 in which the surface area is at least 70 $m^2g^{-1}$.

11. A catalyst according to claim 10 in which the surface area is in the range 80–160 $m^2g^{-1}$.

12. A catalyst according to claim 1 in which the pore volume is in the range 0.2 to 1.0 $cm^3g^{-1}$.

13. A process for producing 1,2-dichloroethane which comprises reacting ethylene with hydrogen chloride and molecular oxygen at a temperature in the range 200°–300° C. and a pressure in the range 1–20 bar abs over a catalyst as defined in claim 1.

* * * * *